(12) United States Patent
Delmas et al.

(10) Patent No.: US 7,015,048 B2
(45) Date of Patent: Mar. 21, 2006

(54) METHODS AND KITS FOR DIAGNOSING OR MONITORING SYNOVIAL OR OSTEOARTICULAR DISEASE, COMPRISING THE USE OF A SPECIFIC MARKER FOR SYNOVIAL TISSUE DEGRADATION

(75) Inventors: Pierre Delmas, Lyons (FR); Patrick Garnero, Villeurbanne (FR); Evelyne Gineyts, Lyons (FR)

(73) Assignee: Institut National de la Sante et de la Recherche Medicale, (FR)

( * ) Notice: Subject to any disclaimer, the term of this patent is extended or adjusted under 35 U.S.C. 154(b) by 0 days.

(21) Appl. No.: 10/038,192

(22) Filed: Jan. 2, 2002

(65) Prior Publication Data

US 2002/0172978 A1 Nov. 21, 2002

Related U.S. Application Data

(63) Continuation of application No. PCT/FR00/01878, filed on Jun. 30, 2000.

(30) Foreign Application Priority Data

Jul. 1, 1999 (FR) .................................. 99 08502

(51) Int. Cl.
  *G01N 33/53* (2006.01)
(52) U.S. Cl. ..................... 436/811; 436/164; 436/172; 436/518; 435/7.1; 435/7.92
(58) Field of Classification Search ................ 436/501, 436/518, 164, 808, 172, 811, 804; 435/7.1, 435/7.92, 810, 967, 7.93–7.94
See application file for complete search history.

(56) References Cited

U.S. PATENT DOCUMENTS

| | | | |
|---|---|---|---|
| 4,444,879 A * | 4/1984 | Foster et al. | 435/7.95 |
| 5,283,197 A * | 2/1994 | Robins | 436/87 |
| 5,420,016 A * | 5/1995 | Boguslaski et al. | 435/12 |
| 5,607,862 A | 3/1997 | Eyre | |
| 5,702,909 A | 12/1997 | Eyre | |
| 5,736,344 A * | 4/1998 | Kung et al. | 435/7.9 |

FOREIGN PATENT DOCUMENTS

| CA | WO 95/02188 | * | 1/1995 |
|---|---|---|---|
| WO | WO-89/12824 A1 | | 12/1989 |

OTHER PUBLICATIONS

St. Clair et al. (A Cross Sectional Analysis of 5 Different Markers of collagen Degradation in rheumatoid Arthritis, The Journal of rheumatology 1998; 25 (8) p. 1472-1479).*
Otsuka et al. (Evaluation of urinary pyridinoline in healthy adults and ptients with rheumatoid arthritis by an improved high performance liuid chromatographic assay., Journal of Nutritional science and Vitaminology (1996), 42 (5) 485-490).*
Black et al. (Urinary Excretion of the Hydroxypyridinium crosslinks of Collagen in Patients with Rheumatoid Arthritis, Ann. rheumat. Dis. 48: 641-644 (1989a).*
Ricard-Blum, S. (1) et al: "Detectable levels of pyridinoline are present in synovial fluid from various patients with knee effusion: Preliminary Results," European Journal of Clinical Investigation (1995) vol. 25, No. 6, pp. 438-441.
Database Biosis Online!, Biosciences Information Service, Philadelphia, PA, Wotton, S.F. (1) et al: Type IX collagen immunoreactive peptides in synovial fluids from arthritis patients, retrieved from STN XP002132753 abstract & Rheumatology (Oxford) (Apr. 1999), vol. 38, No. 4, pp. 338-345.
Database Medline Online!, U.S. National Library of Medicine, Bethesda, MD, Sinigaglia, L. et al.: "Urinary and synovial pyridinium crosslink concentrations in patients with rheumatoid arthritis and osteoarthritis," retrieved from STN Database accession No. 95216979, XP002132754 abstract & Annals of the Rheumatic Diseases (Feb. 1995) 54 (2) 144-7.

* cited by examiner

*Primary Examiner*—Long V. Le
*Assistant Examiner*—Gary W. Counts
(74) *Attorney, Agent, or Firm*—Lerner, David, Littenberg, Krumholz & Mentlik, LLP

(57) ABSTRACT

Disclosed are specific markers for synovial tissue degradation and methods of using the markers in diagnosing, monitoring or determining a prognosis of synovial disease.

13 Claims, 14 Drawing Sheets

FIG 5

| Hydrolysis time | | 5 hours | 10 hours | 15 hours | 20 hours |
|---|---|---|---|---|---|
| Tissue: | | | | | |
| Bone | 1 | - | - | - | - |
| | 2 | - | - | - | - |
| Synovial | 1 | 105% | 94% | 54% | 37% |
| | 2 | 72% | 56% | 64% | 24% |
| Cartilage | 1 | 6% | 2% | 1% | 1% |
| | 2 | 4% | 2% | 2% | 1% |

| Hydrolysis time | | 5 hours | 10 hours | 15 hours | 20 hours |
|---|---|---|---|---|---|
| Tissue: | | | | | |
| Bone | 1 | 56% | 33% | 28% | 24% |
| | 2 | 55% | 44% | 34% | 29% |
| Synovial | 1 | 16% | 12% | 12% | 12% |
| | 2 | 9% | 10% | 9% | 9% |
| Cartilage | 1 | - | - | - | - |
| | 2 | - | - | - | - |

FIG 6

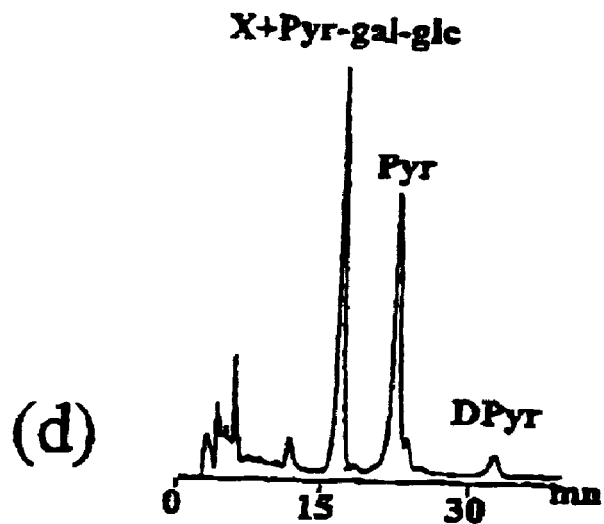
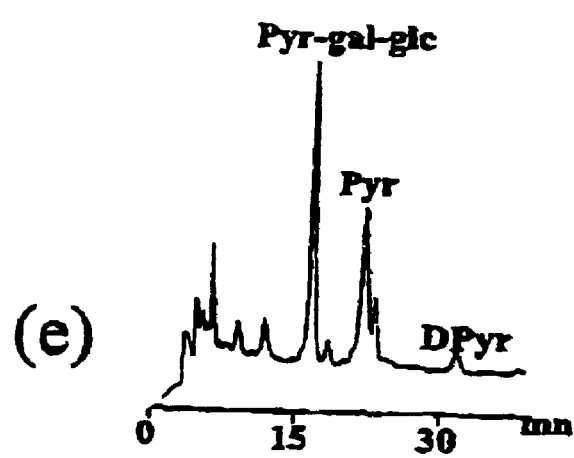
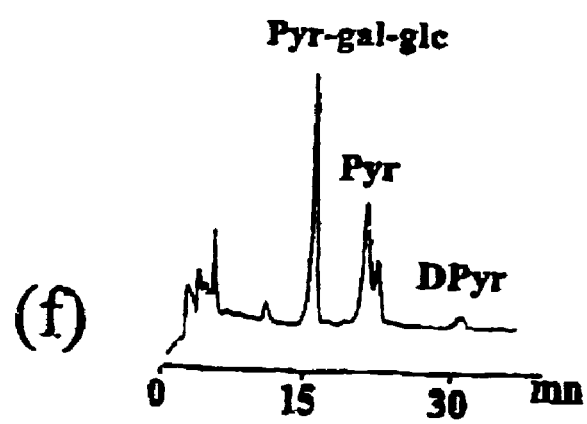
FIG. 7 Cont'd.

| Subjects | n | Age | Total Pyr (nmole/nmole Cr) | | | Free Pyr (nmole/nmole Cr) | | | (nmole/nmole Cr) | |
|---|---|---|---|---|---|---|---|---|---|---|
| | | | Pyr | d-Pyr | Pyr-Gal-Glc | Pyr | D-Pyr | Pyr-Gal-Glc | CartiLaps | CrossLaps |
| Pre-menopausal women | 20 | 35.7 ± 2.8 | 28.5 ± 4.1 | 5.9 ± 1.4 | | 13.4 ± 2.7 | 3.3 ± 0.9 | 4.5 ± 1.0 | 6.2 ± 0.9 | 126 ± 27 |
| Post-menopausal women | 20 | 55.3 ± 2.4 | 34.8 ± 9.5 | 7.6 ± 2.6 | | 15.6 ± 3.7 | 3.7 ± 0.9 | 4.8 ± 1.7 | 7.5 ± 2.8 | 281 ± 100 |
| Controls | 40 | 45.5 ± 10.3 | 31.6 ± 7.9 | 6.7 ± 2.2 | | 14.5 ± 3.4 | 3.5 ± 0.9 | 4.7 ± 1.4 | 6.9 ± 2.2 | 203 ± 106 |
| Rheumatoid arthritis | 27 | 56.2 ± 11.9* | 77.2 ± 51.8* | 10.8 ± 7.6* | | 26.3 ± 15.0* | 4.0 ± 2.3* | 9.6 ± 5.9* | 12.4 ± 8.5* | 266 ± 187* |
| Paget's disease | 10 | | 125.8 ± 53.6* | 31.2 ± 13.5* | | 42.1 ± 15.4* | 10.2 ± 5.1* | 6.1 ± 1.9 | 7.2 ± 2.9 | 834 ± 352* |

* Statistical significance (Anova) $p < 0.05$ of the difference compared with control group.

| | n | Pyr-Gal-Glc (nmole/mmole Cr) | CartiLaps (nmole/mmole Cr) |
|---|---|---|---|
| Controls | 40 | 4.7 ± 1.4 | 6.9 ± 2.2 |
| Rheumatoid arthritis (RA) | 27 | 9.6 ± 5.9* | 12.4 ± 8.5* |
| Destructive RA | 12 | 12.2 ± 7.4* | 16.5 ± 10.0* |
| Non destructive RA | 15 | 7.5 ± 3.2* | 9.2 ± 5.4** |

* Statistical significance (T-test) $p < 0.001$  ** Statistical significance (T-Test) $p < 0.05$

| Pyr-Gal-Glc | Lequesne | Womac | Tibio-femoral space |
|---|---|---|---|
| | 0.42* | 0.50* | -0.50* |

| Progression | Narrowing of joint line | | Bone erosion | | Total score | |
|---|---|---|---|---|---|---|
| | YES (n=27) | NO (n=84) | YES (n=41) | NO (n=70) | YES (n=54) | NO (n=57) |
| Urinary Pyr-Gal-Glc (nmole/nmole creatinine) | 8.8 | 7.2 | 9.3* | 6.5 | 8.8** | 6.3 |

Statistical significance of difference compared with group with no progress * p = 0.03; ** p = 0.05

FIG. 13

METHODS AND KITS FOR DIAGNOSING OR MONITORING SYNOVIAL OR OSTEOARTICULAR DISEASE, COMPRISING THE USE OF A SPECIFIC MARKER FOR SYNOVIAL TISSUE DEGRADATION

CROSS REFERENCE TO RELATED APPLICATIONS

The present application is a continuation of International Application PCT/FR00/01878, filed Jun. 30, 2000, published in French, and which claims priority from French Application No. 99/08502, filed Jul. 1, 1999. The disclosures of said applications are incorporated by reference herein.

BACKGROUND OF THE INVENTION

The present invention relates to a specific marker for synovial tissue degradation and to methods employing this marker in diagnosing, monitoring and determining a prognosis of synovial diseases.

Osteoarticular diseases or joint diseases are characterized by degradation, destruction or resorption of joint tissues. When radiological and clinical symptoms appear, the joint has already undergone major modifications due to attack of the cartilage and bone matrix. The search is on for a marker that can detect an earlier stage of osteoarticular diseases. In this context, the inventors have brought to the fore the fact that synovial tissue is the first to be degraded in certain osteoarticular diseases. In rheumatoid arthritis, the synovial tissue is the first to be degraded, then the cartilage tissue starts to be degraded, and bone tissue is the last to be affected.

SUMMARY OF THE INVENTION

Thus, the identification of specific markers for synovial tissue degradation is of major importance. Since synovial tissue can be one of the first tissues to be attacked in osteoarticular disease, a specific marker for synovial disease can constitute an early marker for osteoarticular disease or a pre-symptomatic marker for osteoarticular disease. Specific synovial markers have not as yet been described in the literature. For the first time, the invention provides a specific marker for synovial tissue, more particularly a marker for synovial collagen degradation. The invention provides a specific marker the level alone of which reflects the degree of degradation of synovial collagen, enabling diagnosis or allowing the evolution of synovial diseases to be monitored. Given that synovial tissue degradation also occurs during osteoarticular diseases, the level of this marker can also provide a diagnosis or monitor the evolution of osteoarticular diseases. Finally, since the inventors have described the degradation of synovial tissue as an early stage of osteoarticular diseases, this marker is also a pre-symptomatic marker for osteoarticular diseases.

Preferably, a specific marker for synovial disease in accordance with the invention is glycosylated pyridinoline, more particularly diglycosylated pyridinoline (Pyr-Gal-Glc), also known as glucosyl-galactosyl-pyridinoline or disaccharide pyridinoline. The present inventors have identified Pyr-Gal-Glc as a specific marker for the degradation of synovial collagen.

The pyridinoline molecule results from the condensation of three hydroxylysine residues one of which originates from the helical region of the collagen molecule (major type: type I for bone tissue, type I and III for synovial tissue, type II for cartilage tissue) with the two others originating from C and N terminal telopeptides (see FIG. 1). The hydroxylysine residues can be glycosylated by adding sugar at the hydroxyl group. Then, if pyridinoline formation involves a glycosylated hydroxylysine residue, a glycosylated pyridinoline will be produced (see FIGS. 2c and 2d)). In contrast, deoxypyridinoline (see FIG. 2b)), which is formed via a lysine residue, cannot be glycosylated because the hydroxyl group is absent from the side chain that comprises the hydroxyl group in the pyridinoline form.

Diglycosylated pyridinoline was recorded in the urine from patients with osteoporosis (Robins S P et al., $3^{rd}$ Int. Sym. On Osteoporosis, Copenhagen, p. 465, edited by C. Christiansen and K. Overgaard, 1990).

The use of diglycosylated pyridinoline has also been suggested as an index for resorption of bone collagen and cartilage collagen and along with the measurement of both diglycosylated pyridinoline and monoglycosylated pyridinoline as an indicator of arthritic disease (International patent application WO-A-89/12824).

The invention has demonstrated that diglycosylated pyridinoline is not a resorption index for bone collagen or for cartilage collagen but an indication of synovial disease, and an increase in diglycosylated pyridinoline in biological fluids is an indication of osteoarticular disease but not of bone disease.

Within the context of the invention, the inventors have characterized the major type of pyridinoline glycosylation in the bone matrix, in cartilage and in synovia (see FIGS. 3 to 7). The different forms of pyridinoline in bone, cartilage and synovia have been studied in an ex vivo tissue degradation model.

Within the context of the invention, the existence of glycosylated forms of pyridinoline has been demonstrated in urine, along with the importance of their assay in the study of osteoarticular diseases such as rheumatoid arthritis or arthrosis. The variation in the proportions of each pyridinoline or deoxypyridinoline form (total, free, mono- or diglycosylated) in "model" diseases, i.e., characterized either by a specific and intense increase in bone remodelling (Paget's disease), or by inflammation of the synovia with cartilage attack (arthrosis, rheumatoid arthritis) has been analysed. For the first time, the present invention demonstrates a direct link between inflammation and degradation of the synovia. Total pyridinolines and deoxypyridinolines were measured after acid hydrolysis. Free pyridinolines and deoxypyridinolines were measured after alkaline hydrolysis for tissues and without hydrolysis for supernatants. These results are shown in FIGS. 3 to 7. These results show that the diglycosylated pyridinoline marker (Pyr-Gal-Glc) is specific for a synovial disease or for synovial degradation and can be correlated with a known specific marker (CartiLaps) for cartilage disease or for cartilage degradation (see FIG. 10).

Further, in the context of the invention, the importance of assaying glycosylated forms of pyridinoline has been demonstrated, more particularly the diglycosylated form in urine to monitor the evolution of osteoarticular diseases (see FIGS. 8 and 9). The more advanced the disease in an individual or the more the individual is characterized by a grave form of the disease, the more Pyr-Gal-Glc marker is found in urine, correlating with that which can be measured with a known marker such as CartiLaps. The quantity of Pyr-Gal-Glc measured in an individual at the destructive stage is higher than that measured in an individual at the non-destructive stage (FIG. 11). Further, in an individual with an osteoarticular disease, a large quantity of Pyr-Gal- Glc in the urine indicates an increased risk of evolution towards a rapid joint destruction stage (FIG. 13).

Determining urinary excretion of the two pyridinoline glycosylation forms constitutes specific markers for the degradation of the bone matrix, cartilage and synovia. The specificity of the bone, cartilage and synovial tissue with respect to the skin is provided by the pyridinoline ring (type I collagen in the skin is only slightly bridged by pyridinoline) and tissue specificity (synovial, cartilage, bone) is provided by glycosylation and the type of glycosylation. An increase in the quantity of disaccharide pyridinoline corresponds to an increase in the degradation of collagen of synovial origin, to inflammation of the synovia or to proliferation of collagen of synovial origin; an increase in the quantity of monosaccharide pyridinoline corresponds to a degradation in collagen of bone origin, while an increase in the quantity of pyridinoline and the absence of glycosylated pyridinoline corresponds to a degradation of collagen of cartilage origin.

BRIEF DESCRIPTION OF THE DRAWINGS

FIG. 4(d) corresponds to the chromatogram for urine.

Pyr and D-Pyr represent the hydroxy and deoxy forms of non glycosylated pyridinoline respectively. Compound X present in the synovial tissue but not in bone tissue co-migrates with the standard Pyr-Gal-Glc purified from urine. Compound Y present in bone and in a very small quantity in synovial tissue does not co-migrate with standard Pyr-Gal-Glc purified from urine.

FIG. 5 is a table showing percentage of Pyr-Gal-Glc/free Pyr present in human synovial, bone and cartilage tissue measured by reverse phase column HPLC after hydrolysis with 2M NaOH for times varying from 5 to 20 hours. The symbol "-" means undetectable.

FIG. 6 is a table showing percentage of Pyr-Gal/free Pyr present in human synovial, bone and cartilage tissue measured by reverse phase column HPLC after hydrolysis with 2M NaOH for times varying from 5 to 20 hours. The symbol "-" means undetectable.

FIGS. 7a–f are chromatograms of (a) synovia culture supernatant, (b) bone culture supernatant, (c) cartilage culture supernatant (d) synovia culture supernatant supplemented with standard Pyr-Gal-Glc, Pyr and D-Pyr, (e) bone culture supernatant supplemented with standard Pyr-Gal-Glc, Pyr and D-Pyr, and (f) cartilage culture supernatant supplemented with standard Pyr-Gal-Glc, Pyr and D-Pyr. Compound X in the synovia culture supernatant co-migrates with standard Pyr-Gal-Glc purified from urine and is transformed into Pyr after acid hydrolysis.

FIG. 8 is a table showing urinary excretion of total pyridinolines (free and peptide forms) and free pyridinoline forms in normal adults (controls) and in patients with rheumatoid arthritis or Paget's disease. "Total Pyr" means total pyridinoline or total deoxypyridinoline. "Free Pyr" means free pyridinoline or free deoxypyridinoline.

Figure 9:
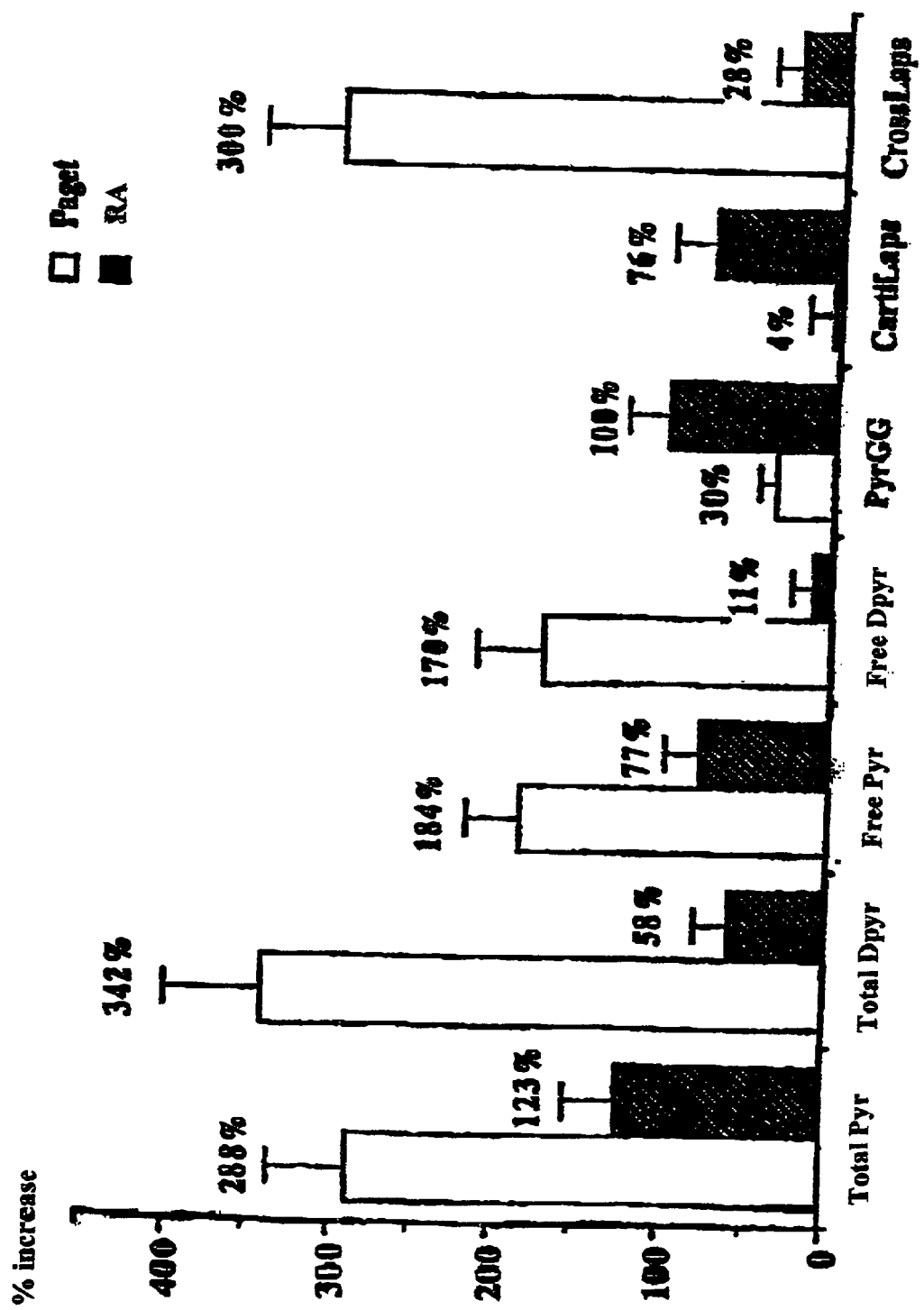

FIG. 9 is a bar graph showing percentage increase in urinary excretion of different markers in rheumatoid arthritis (RA) and in Paget's disease (Paget) compared with a control group (see FIG. 8). "PyrGG" means Pyr-Gal-GLc or diglycosylated pyridinoline.

Figure 10:
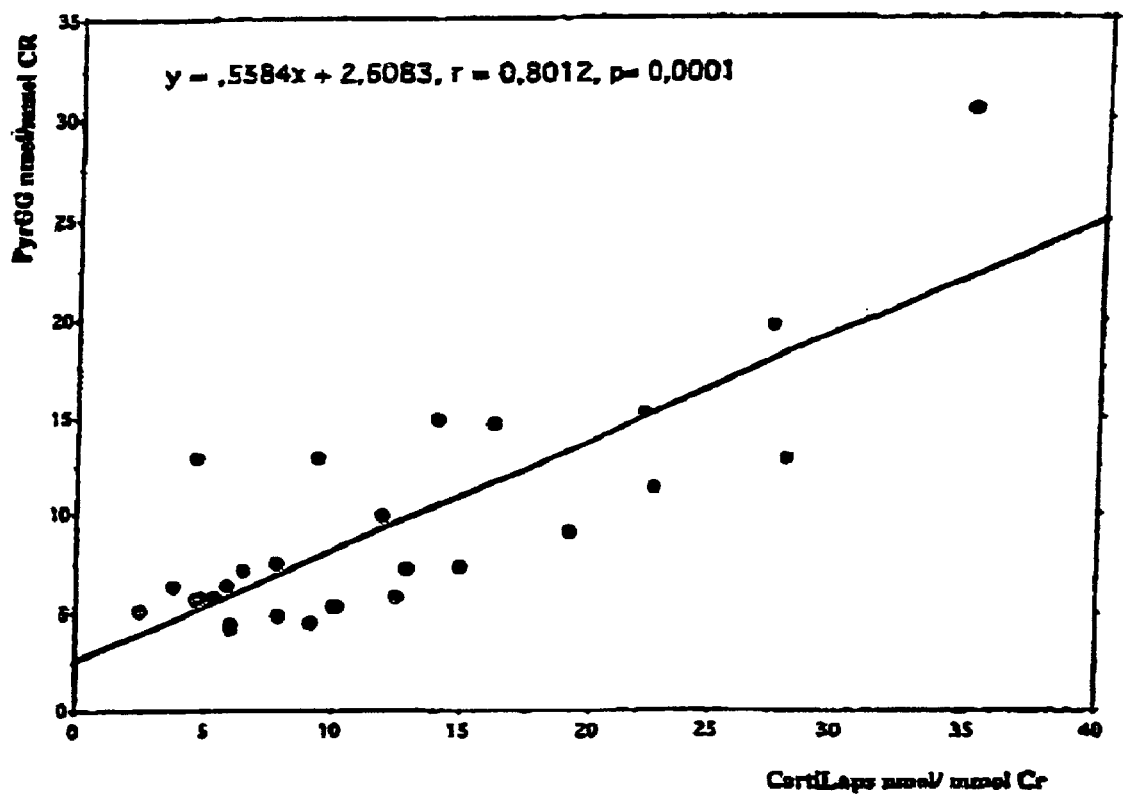

FIG. 10 is a graph showing linear correlation between a specific marker for cartilage (CartiLaps) and diglycosylated pyridinoline (PyrGG).

FIG. 11 is a table showing comparison of quantity of diglycosylated pyridinoline (Pyr-Gal-Glc) measured in normal individuals or patients with rheumatoid arthritis (RA) at a destructive stage (destructive RA) or non destructive stage (non destructive RA).

FIG. 12 is a table showing correlation between urinary excretion of Pyr-Gal-Glc, Lequesne and Womac algofunctional indices and joint line (tibio-femoral space) in 50 patients with gonarthrosis.

FIG. 13 is a table showing correlation between the base level of urinary Pyr-Gal-Glc measured by HPLC and the risk of rapid destruction of joints in the following year by X ray examination of hands and feet in 112 patients with rheumatoid arthritis for less than three years.

DETAILED DESCRIPTION OF THE INVENTION

Definitions diglycosylated pyridinoline is designated by the abbreviation Pyr-Gal-Glc and is also termed glucosyl-galactosyl-pyridinoline or disaccharide pyridinoline;

an "individual" may belong to one or more of the following categories:
 a. an individual who may develop a synovial disease;
 b. a model for a given disease and in particular a model used in pre-clinical studies;
 c. a human being;
 d. a patient;
 e. a patient or individual undergoing medical treatment or surgical intervention;
 f. an individual who is or has been treated for an osteoarticular disease;
 g. an individual with a synovial disease or suspected of developing such a disease;
 h. an individual with an osteoarticular disease;
 i. an individual not suffering from an osteoporosis;
 j. an individual in the growth period;
 k. a male individual;
 l. a female individual;
 m. a child;
 n. an adult;
 o. a pre- or post-menopausal female individual;

p. an animal such as a rat, mouse, rabbit, sheep, primate or racehorse;

a "specific marker for synovial disease" means a substance or compound that can distinguish between a synovial disease and other diseases and in particular a bone and/or cartilage affliction. Preferably, the specific marker for synovial disease is a marker for synovial collagen degradation;

a "synovial disease" means an increase in turn-over, proliferation, degradation, inflammation, destruction, decomposition, pathological remodelling or degradation of the synovia or synovial collagen;

"synovial collagen" means a type I, III, IV, V, or VI collagen or a mixture of collagens selected from said collagens. Preferably, it is mainly a type I and III collagen;

an "osteoarticular disease" means a disease of one or more joints or which involves proliferation of the synovia and cartilage attack. An osteoarticular disease can be inflammatory rheumatism, a metabolic arthropathy or degenerative rheumatism, rheumatoid arthritis, spondylarthritis, gout, chondrocalcinosis or arthrosis;

a "biological sample" means a body fluid. The body fluid is generally removed from the individual before carrying out a method in accordance with the invention. The body fluid can be selected from blood, serum, plasma, urine, saliva, sweat or synovial fluid. The synovial fluid is advantageous, provided that it is specific to the synovial tissue or from the synovia. A biological sample can be a tissue removed from an individual. The tissue can be cultured before carrying out any measurements or determinations with this tissue. The tissue may be the synovia;

the "destructive stage" of an osteoarticular disease corresponds to the stage at which destruction or degradation of the joint tissues can be observed by radiography, magnetic resonance or nuclear magnetic resonance. The "non destructive" stage corresponds to the stage at which destruction or degradation of the joint tissues is still not visible by radiography, magnetic resonance or nuclear magnetic resonance;

"free pyridinoline" means pyridinoline not bound to any peptide;

"glycosylated pyridinoline" means pyridinoline carrying glycosylated groups. "Glycosylated pyridinoline" means both glycosylated pyridinoline carrying peptide residues and glycosylated pyridinoline free of peptide. According to the technique employed to measure glycosylated pyridinoline, and according to the technique employed in preparing the biological sample (alkaline hydrolysis or absence of hydrolysis), the method of the invention can exclusively measure free glycosylated pyridinoline, or alternatively total glycosylated pyridinoline.

The methods of the invention described below can be qualitative or quantitative techniques, or both quantitative and qualitative. The methods described in the remainder of the text in which a variation in the quantity of a specific marker is detected can be considered to be quantitative methods. The methods described in the remainder of the text in which the presence of a specific marker is detected can be considered to be qualitative methods.

In general, the invention concerns a method for monitoring the degradation of synovial collagen in an individual. Synovial collagen degradation can be normal (i.e., non-pathological, in the context of normal synovial turnover) or it can be pathological. The methods of the invention are particularly advantageously applicable in monitoring, diagnosis and prognosis of synovial diseases and in evaluating the efficacy of therapeutic treatments.

More particularly, the invention concerns a method for diagnosis, possibly early diagnosis, or for monitoring the evolution of an osteoarticular disease involving synovial collagen degradation. This method is characterized by:
i) bringing a biological sample from an individual into contact, in vitro, with a means for measuring a specific marker for the level of degradation of synovial collagen;
ii) determining the level of the specific marker.

Preferably, the marker is a marker the level alone of which reflects the level of synovial collagen degradation.

In a first aspect, the invention concerns a method for diagnosing or monitoring the evolution of a synovial disease, characterized by:
i) bringing a biological sample from an individual into contact, in vitro, with a means for measuring a specific marker for synovial disease;
ii) determining the level of the specific marker;
iii) optionally, comparing the level of the marker with a reference level representing the absence of the disease or representing a predetermined stage in the disease, the level of the marker with respect to the reference level indicating the presence of or evolution of the synovial disease.

A method in accordance with this aspect of the invention enables positive or negative changes in the evolution of a synovial disease to be detected, and allows the appearance or termination of the disease to be detected.

The preferred individual for the first aspect of the invention has a synovial disease or is capable of developing a synovial disease, i.e., may or may not present with symptoms of synovial disease.

The preferred specific marker for synovial disease is glycosylated pyridinoline, more particularly diglycosylated pyridinoline.

In the diagnostic application of the method according to the first aspect of the invention, the reference level representing the absence of disease or representing a pre-determined stage of the disease can be selected as a function of the mean value or maximum value measured for the specific marker in a sample of individuals who do not suffer from disease.

The choice of reference level for the diagnostic application of the method according to the first aspect of the invention can be determined by the skilled person as a function of the selected specific marker for synovial disease and of the technique used to measure the specific marker for synovial disease.

If the selected marker is diglycosylated pyridinoline and the technique is HPLC, the reference level that delimits the disease state from the non-disease state can be in the range of values from about 5 (nmoles/mmoles creatinine) to about 9 (nmoles/mmoles creatinine).

When applying the method for monitoring the evolution of a synovial disease in accordance with the first aspect of the invention, the reference level can correspond to the limit between the non disease state and the disease state for a synovial disease or to the limit between two distinct stages in the evolution of the synovial disease. Two distinct stages in the evolution of a synovial disease can be the non-destructive stage and the destructive stage.

The limit between two distinct stages in the evolution of a synovial disease can be selected to be between values in the range from the mean value plus one standard deviation to the mean value plus three standard deviations measured for a representative control sample of non diseased individuals who do not have a synovial disease. A particularly pertinent value is that of the mean value plus two standard deviations.

The limit between two distinct stages in the evolution of a synovial disease can be selected in the range between the mean value plus one standard deviation and the mean value plus three standard deviations measured for a representative sample of individuals who are in the least advanced stage of the two distinct stages in the evolution of a synovial disease. A particularly pertinent value is that of the mean value plus two standard deviations.

The reference level for the specific marker can be the anteriorly measured level in the same individual.

The choice of reference level for monitoring the evolution of a synovial disease in accordance with the first aspect of the invention can be determined by the skilled person as a function of the selected specific marker for synovial disease and of the technique used to measure said specific marker.

If the selected marker is diglycosylated pyridinoline and the technique is HPLC, the reference level that delimits two distinct stages of the disease, in particular the non-destructive stage from the destructive stage, can be in the range of values from about 5 (nmoles/mmoles creatinine) to about 9 (nmoles/mmoles creatinine).

The invention also concerns a kit for diagnosing or monitoring the evolution of a synovial disease, characterized in that it comprises at least one means for measuring a specific marker for synovial disease and mentions the reference level representing the absence of disease or representing a pre-determined stage of the disease.

In a preferred variation of the invention, the synovial disease is an osteoarticular disease. In this second aspect, the invention concerns a method for monitoring the evolution of an osteoarticular disease, characterized by:
  i) bringing a biological sample from an individual into contact, in vitro, with a means for measuring a specific marker for synovial disease;
  ii) determining the level of the specific marker;
  iii) optionally, comparing the level of the marker with a reference level representing a predetermined stage in the disease, the level of the marker with respect to the reference level indicating the evolution of the osteoarticular disease.

A method in accordance with this second aspect of the invention enables positive or negative changes in the progress of an osteoarticular disease to be detected, as well as the appearance or end of such a disease.

The preferred individual in this aspect of the invention already has an osteoarticular disease.

The invention also concerns a kit for diagnosing or monitoring the evolution an osteoarticular disease, characterized in that it comprises at least one means for measuring a specific marker for synovial disease and mentions the reference level representing the absence of disease or representing a pre-determined stage of the disease.

The preferred specific marker for synovial disease in this variation is again glycosylated pyridinoline, more particularly diglycosylated pyridinoline.

The reference level for the method and the kit of the second aspect of the invention can correspond to the limit between the non-disease state and the disease state or to the limit between two distinct stages in the evolution of the disease. Two distinct stages in the evolution of an osteoarticular disease can be the non-destructive stage and the destructive stage.

The limit between the disease stage and the non disease stage of an osteoarticular disease can be selected between values in the range from the mean value plus one standard deviation to the mean value plus three standard deviations measured for a representative control sample of non diseased individuals or those who do not have an osteoarticular disease. A particularly pertinent value is that of the mean value plus two standard deviations.

The limit between two distinct stages in the evolution of an osteoarticular disease can be selected in the range between the mean value plus one standard deviation to the mean value plus three standard deviations measured for a representative control sample of non diseased individuals or those who do not have an osteoarticular disease. A particularly pertinent value is that of the mean value plus two standard deviations.

The limit between two distinct stages in the evolution of an osteoarticular disease is selected in the range between the mean value plus one standard deviation to the mean value plus three standard deviations measured for a representative sample of individuals who are in the least advanced stage of two distinct stages in the evolution of an osteoarticular disease. A particularly pertinent value is that of the mean value plus two standard deviations.

The reference level for the method and kit of the second aspect of the invention can be the anteriorly measured level in the same individual.

The choice of the reference level for the method and kit according to the second aspect of the invention can be determined by the skilled person as a function of the selected specific marker for synovial disease and of the technique used to measure said specific marker.

If the selected marker is diglycosylated pyridinoline and the technique is HPLC, the reference level that delimits the non disease state from the disease state can be in the range from about 5 (nmoles/mmoles creatinine) to about 9 (nmoles/mmoles creatinine).

If the selected marker is diglycosylated pyridinoline and the technique is HPLC, the reference level that delimits two distinct stages in the evolution of an osteoarticular disease can be in the range from about 5 (nmoles/mmoles creatinine) to about 9 (nmoles/mmoles creatinine).

In a third aspect, the invention concerns a prognostic method for determining the evolution towards an osteoarticular disease or towards a stage in osteoarticular disease. The inventors have determined that the level of a specific marker for synovial degradation, for example diglycosylated pyridinoline, in an individual can indicate, by reference to a pre-determined reference, the risk that individual runs of suffering accelerated joint destruction. This method is characterized by:
  i) bringing a biological sample from an individual into contact, in vitro, with a means for measuring a specific marker for synovial disease;
  ii) determining the level of the specific marker;
  iii) optionally, comparing the level of the marker with a reference level and deducing a prognosis of evolution towards an osteoarticular disease or towards a stage in osteoarticular disease.

The preferred individual in this third aspect of the invention has osteoarticular disease or is susceptible of developing an osteoarticular disease.

In this aspect of the invention, the preferred specific marker for synovial disease is glycosylated pyridinoline, more particularly diglycosylated pyridinoline.

The invention also concerns a diagnostic kit for determining a prognosis of evolution towards an osteoarticular disease or towards a stage in osteoarticular disease, characterized in that it comprises at least one means for measuring a specific marker for synovial disease and mentions the reference level representing a prognosis.

The method or kit of the third aspect of the invention can provide a prognosis of evolution towards an osteoarticular disease for an individual showing no signs of osteoarticular disease, or towards a stage in osteoarticular disease, in particular the destructive stage, for an individual in the non-destructive stage of osteoarticular disease.

In particular, the prognosis that can be determined using a method or kit in accordance with the third aspect of the invention can cover a period of 1, 2, 3, 4 or 5 years.

The reference level for a method or kit in accordance with the third aspect of the invention can be determined by a longitudinal study of a sample of individuals at risk of osteoarticular disease or individuals in a non destructive stage of osteoarticular disease. The reference level for the method described above can also be determined by analysing existing samples removed from a single individual at different times.

In a fourth aspect, the invention concerns a method for determining the efficacy of a drug administered to an individual for the treatment of an osteoarticular disease, characterized by:
  i) bringing a biological sample from an individual under treatment into contact, in vitro, with a means for measuring a specific marker for synovial disease;
  ii) determining the level of the specific marker;
  iii) optionally, comparing the level of the marker with a reference level representing a predetermined stage in the disease, the level of the marker with respect to the reference level indicating the evolution of the synovial disease, and therefore the efficacy of the treatment.

The preferred individual in this fourth aspect of the invention is an animal used as a model in preclinical studies of the efficacy of a given treatment for an osteoarticular disease, or it can be a human in whom the treatment is being monitored.

The invention also concerns a kit for determining the efficacy of a drug administered to an individual for the treatment of an osteoarticular disease, characterized in that it comprises at least one means for measuring a specific marker for synovial disease and mentions the reference level representing the efficacy of the drug.

In this fourth aspect of the invention, the preferred specific marker for synovial disease is glycosylated pyridinoline, more particularly diglycosylated pyridinoline.

The treatment can be curative or prophylactic.

The reference level in this fourth aspect of the invention can be the anteriorly measured level in the same individual. The anteriorly measured level is preferably measured before the start of curative or prophylactic treatment of an osteoarticular disease or before administering a drug intended to treat an osteoarticular disease.

The reference level in this fourth aspect of the invention can correspond to the limit between the non-disease state and the disease state for an osteoarticular disease or to the limit between two distinct stages in the evolution of the osteoarticular disease. The two distinct stages in the evolution of an osteoarticular disease can be the non-destructive stage and the destructive stage.

The limit between the disease stage and the non disease stage of an osteoarticular disease can be selected between values in the range from the mean value plus one standard deviation to the mean value plus three standard deviations measured for a representative control sample of non diseased individuals or who do not have a osteoarticular disease. A particularly pertinent value is that of the mean value plus two standard deviations.

The limit between two distinct stages in the evolution of an osteoarticular disease can be selected in the range between the mean value plus one standard deviation to the mean value plus three standard deviations measured for a representative control sample of non diseased individuals or who do not have osteoarticular disease. A particularly pertinent value is that of the mean value plus two standard deviations.

The limit between two distinct stages in the evolution of an osteoarticular disease can be selected in the range between the mean value plus one standard deviation and the mean value plus three standard deviations measured for a representative sample of individuals who are in the least advanced stage of the two distinct stages of the evolution of an osteoarticular disease. A particularly pertinent value is that of the mean value plus two standard deviations.

The choice of the reference level for this fourth aspect of the invention can be determined by the skilled person as a function of the selected specific marker for synovial disease and of the technique used to measure said specific marker.

If the selected marker is diglycosylated pyridinoline and the technique is HPLC, the reference level that delimits the non disease state from the disease state for an osteoarticular disease can be in the range from about 5 (nmoles/mmoles creatinine) to about 9 (nmoles/mmoles creatinine).

If the selected marker is diglycosylated pyridinoline and the technique is HPLC, the reference level that delimits two distinct stages in the evolution of an osteoarticular disease can be in the range from about 5 (nmoles/mmoles creatinine) to about 9 (nmoles/mmoles creatinine).

The efficacy of the curative or prophylactic treatment deduced from the method or kit of the fourth aspect of the invention can be positive, zero or negative.

If comparison of the level of the marker measured with the reference level shows a tendency of the condition of the individual studied to improve, it can then be concluded that the curative or prophylactic treatment used for that individual has at least the beginnings of efficacy. The difference between the level of the marker measured in the individual and the reference level enables the efficacy of the curative or prophylactic treatment being tested to be determined qualitatively or quantitatively.

The efficacy of a curative treatment (cure) or a prophylactic treatment (prevention) of an osteoarticular disease can then be correlated with a measurement of the variation in the quantity of a specific marker for synovial disease.

In a fifth aspect, the invention concerns a method for determining the toxicity associated with an osteoarticular or synovial disease of a drug intended to treat a disease. Certain drugs can cause secondary effects on the synovial level and in particular, can lead to a degradation of synovial collagen. According to this aspect of the invention, the method is characterized by:
  i) bringing a biological sample from an individual into contact, in vitro, with a means for measuring a specific marker for synovial disease;
  ii) determining the level of the specific marker;
  iii) optionally, comparing the level of this marker with a reference level representing the presence or a predetermined stage in the disease, the level of the marker with respect to the reference level indicating the degree of the disease and therefore, the degree of toxicity associated with a synovial or osteoarticular disease.

The invention also concerns a diagnostic kit for determining the toxicity of a drug intended to treat a disease, characterized in that it comprises at least one means for measuring a specific marker for synovial disease and mentions the reference level representing a level of toxicity of the drug.

The term "drug" means any pharmaceutical composition the toxicity of which in an individual is capable of being associated with or expressed by a synovial disease or an osteoarticular disease.

The reference level in this fifth aspect of the invention can correspond to the limit between the non-disease state and the disease state for an osteoarticular disease or to the limit between two distinct stages in the evolution of the osteoarticular disease. Two distinct stages in the evolution of an osteoarticular disease can be the non-destructive stage and the destructive stage.

The limit between the disease stage and the non disease stage of an osteoarticular disease can be selected between values in the range from the mean value plus one standard deviation to the mean value plus three standard deviations measured for a representative control sample of non diseased individuals or those who do not have osteoarticular disease. A particularly pertinent value is that of the mean value plus two standard deviations.

The limit between two distinct stages in the evolution of an osteoarticular disease can be selected in the range between the mean value plus one standard deviation to the mean value plus three standard deviations measured for a representative control sample of non diseased individuals or those who do not have an osteoarticular disease. A particularly pertinent value is that of the mean value plus two standard deviations.

The limit between two distinct stages in the evolution of an osteoarticular disease can be selected in the range between the mean value plus one standard deviation to the mean value plus three standard deviations measured for a representative control sample of individuals who are in the least advanced stage of two distinct stages in the evolution of an osteoarticular disease. A particularly pertinent value is that of the mean value plus two standard deviations.

The reference level in this fifth aspect of the invention can be the anteriorly measured level in the same individual. The anteriorly measured level is preferably measured before commencement of curative or prophylactic treatment or before administering a drug.

The choice of the reference level in this fifth aspect of the invention can be determined by the skilled person as a function of the selected specific marker for synovial disease and of the technique used to measure said specific marker.

If the selected marker is diglycosylated pyridinoline and the technique is HPLC, the reference level that delimits the non disease state from non disease state of an osteoarticular disease can be in the range from about 5 (nmoles/mmoles creatinine) to about 9 (nmoles/mmoles creatinine).

If the selected marker is diglycosylated pyridinoline and the technique is HPLC, the reference level that delimits two distinct stages in the evolution of an osteoarticular disease can be in the range from about 5 (nmoles/nmoles creatinine) to about 9 (nmoles/nmoles creatinine).

The toxicity of the curative or prophylactic treatment deduced from the method of this fifth aspect of the invention may exist, or it may be zero.

If comparison of the level of the marker measured with the reference level shows the appearance of synovial or osteoarticular disease, it can then be concluded that the curative or prophylactic treatment used for that individual has at least some toxicity. The difference between the level of the marker measured in the individual and the reference level enables the toxicity of the curative or prophylactic treatment being tested to be determined qualitatively or quantitatively.

Some treatments or drugs produce a synovial disease or osteoarticular disease as a toxic effect. Detecting such diseases can thus detect the toxicity of a treatment or drug.

In a sixth aspect, the invention concerns a method for early diagnosis of an osteoarticular disease, characterized by:
 i) bringing a biological sample from an individual into contact, in vitro, with a means for measuring a specific marker for synovial disease;
 ii) determining the level of the specific marker;
 iii) optionally, comparing the level of the marker with a reference level representing the presence of the disease, the level of the marker with respect to the reference level indicating the actual or potential presence of synovial disease.

Since synovial tissue is one of the first to be attacked in an osteoarticular disease, for example rheumatoid arthritis, a method according to this sixth aspect of the invention constitutes a means for early, pre-symptomatic detection or detection before the destructive phase of an osteoarticular disease.

The invention also concerns a kit for early diagnosis of synovial disease, characterized in that it comprises at least one means for measuring a specific marker for synovial disease and mentions the reference level representing the absence of disease.

The preferred individual in this sixth aspect of the invention has an osteoarticular disease or is capable of developing an osteoarticular disease.

In this sixth aspect of the invention, the preferred specific marker for synovial disease is glycosylated pyridinoline, more particularly diglycosylated pyridinoline.

The reference level in this sixth aspect of the invention can correspond to the limit between the non disease state and the disease state for an osteoarticular disease.

The limit between the disease stage and the non disease stage of an osteoarticular disease can be selected between values in the range from the mean value plus one standard deviation to the mean value plus three standard deviations measured for a representative control sample of non diseased individuals or those who do not have an osteoarticular disease. A particularly pertinent value is that of the mean value plus two standard deviations.

The choice of the reference level in this sixth aspect of the invention can be determined by the skilled person as a function of the selected specific marker for synovial disease and of the technique used to measure said specific marker for synovial disease.

If the selected marker is diglycosylated pyridinoline and the technique is HPLC, the reference level that delimits the disease state from the non-disease state for an osteoarticular disease can be in the range from about 5 (nmoles/mmoles creatinine) to about 9 (nmoles/mmoles creatinine).

In all of the methods or kits of the invention, the specific marker for synovial disease can be measured by an immunological technique, by immunoassay, by fluorescence, by ultraviolet spectroscopy or by electrochemical detection.

The terms "immunological technique" or "immunoassay" may mean a technique employing specific monoclonal or polyclonal antibodies, an ELISA technique, an immuno-enzymatic technique, an immunofluorescence technique, a radio-immunological technique, an electrochemo-immunological technique or a chemo-immunological technique.

The terms "immunological technique" or "immunoassay" can mean any one of the techniques described in the following publication: Diamandis and Cristopoulos, Immunoassay, Academic Press, San Diego, 1996, in particular pages 579 ff.

Preferably, the level of the specific marker is measured using a biological sample that has not undergone prior acid or alkaline hydrolysis, particularly when the sample is urine.

The preferred specific marker for synovial disease is glycosylated pyridinoline, more particularly diglycosylated pyridinoline.

Preferably, the glycosylated pyridinoline or diglycosylated pyridinoline is bound to one or more specific peptides for synovial collagen, type I collagen, type III collagen, type IV collagen, type V collagen, type VI collagen, type I and III collagen or a mixture of collagens selected from types I, III, IV, V and VI.

The diglycosylated form of pyridinoline is advantageously purified and characterized using the method described in Example 3 of the present application.

The isolated or purified glucosyl-galactosyl-pyridinoline can be used to produce antibodies in an individual.

One preferred means for measuring a specific marker for synovial disease is an antibody that can specifically recognise a specific marker for synovial disease and in particular glucosyl-galactosyl-pyridinoline.

The invention also concerns an antibody that can specifically recognise glucosyl-galactosyl-pyridinoline.

The term "specifically recognise glucosyl-galactosyl-pyridinoline" may mean the capacity to distinguish glucosyl-galactosyl-pyridinoline from other pyridinoline derivatives not comprising the disaccharide or glucosyl-galactosyl portion of the glucosylgalactosyl-pyridinoline. Preferably, the antibodies of the invention do not cross-react with pyridinoline derivatives other than the diglycosylated derivative.

The antibodies of the invention can be monoclonal or polyclonal and preferably recognise one or more epitopes unique to the diglycosylated form of pyridinoline. It may be free diglycosylated pyridinoline (no peptide) or diglycosylated pyridinoline bound to peptide residues, or both forms.

The invention concerns the antibodies produced or capable of being produced from isolated or purified glucosyl-galactosyl-pyridinoline, in particular from the glucosyl-galactosyl-pyridinoline isolated according to the invention.

The antibodies of the invention defined above constitute preferred means for measuring a specific marker for synovial disease.

The antibodies of the invention defined above can be obtained using any current technique for producing an antibody from a specific marker for synovial disease and in particular glucosyl-galactosyl-pyridinoline.

The production of a specific antibody for glucosyl-galactosyl-pyridinoline may necessitate that said antigen is initially extracted and purified from urine, for example. Such extraction or purification can advantageously be carried out using the technique described in Example 3 of the present application.

EXAMPLES

Example 1

Pyridinoline Glycosylation Type Study in Bone, Cartilage and Synovial Tissue.

Method:

The human tissues originated from bone, cartilage and synovia collected during surgical intervention for hip replacement. The tissue samples were finely ground in liquid nitrogen then divided into 10 mg aliquots and hydrolysed with 2M NaOH at 110° C. The hydrolysis times were between 5 and 24 hours. In contrast to acid hydrolysis, which releases the sugars bound to the pyridinolines, alkaline hydrolysis releases pyridinoline molecules from collagen without affecting the galactose and glucose residues that may be present. After alkaline hydrolysis, free pyridinolines were extracted by partition chromatography on a cellulose column. Separation and quantification of different forms of glycosylated pyridinolines are carried out by reverse phase column HPLC on an ultrasphere ODS Beckman (5 mm, 25 cm×4.6 mm) at a flow rate of 1 ml/minute using a solution containing 6% acetonitrile and 0.15% heptafluorobutyric acid. They were detected using natural fluorescence at respective excitation and emission wavelengths of 297 nm and 395 nm.

Figure 1:
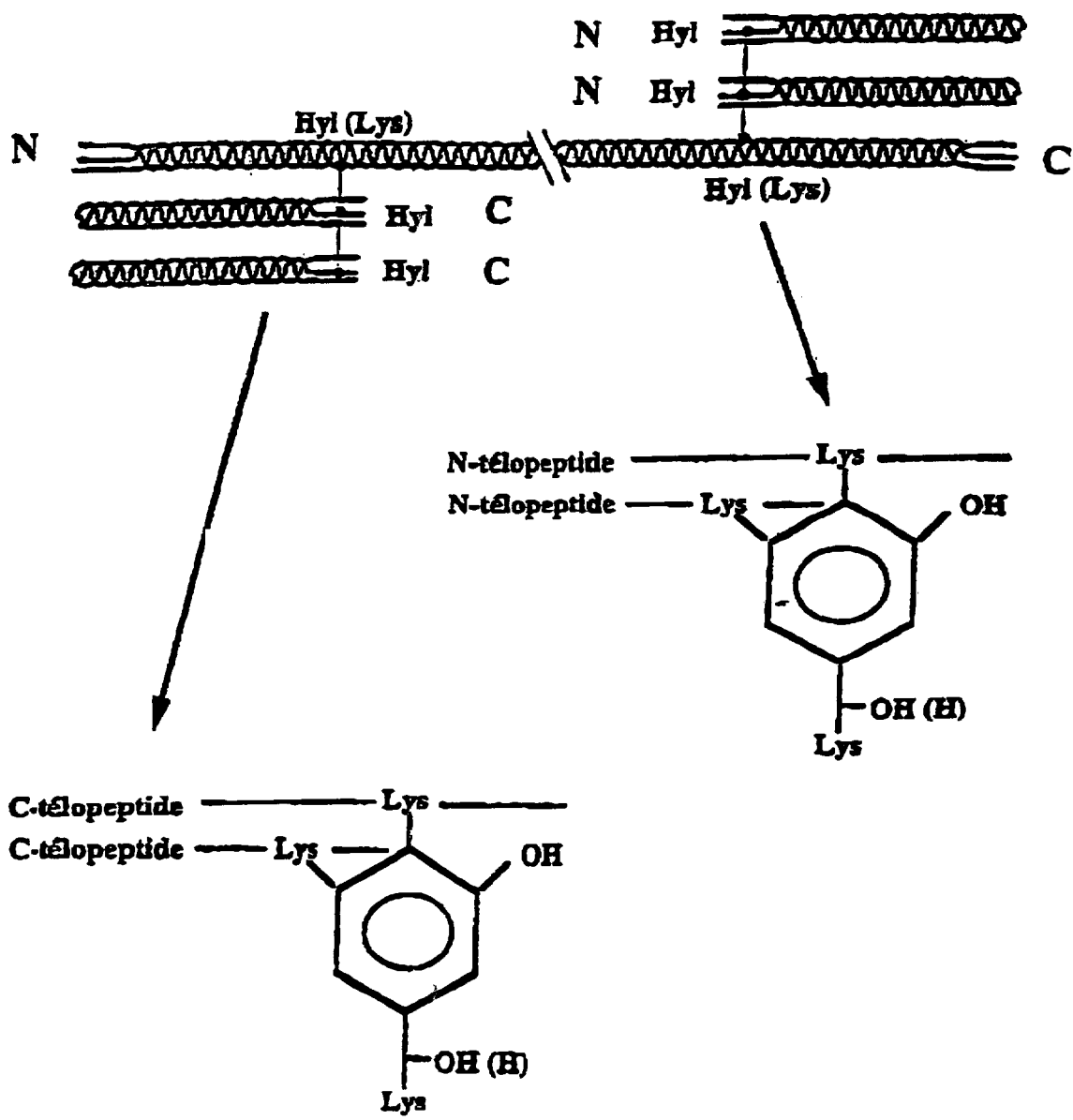
FIG. 1 is a schematic representation of pyridinoline molecules enabling collagen bridging.
Figure 2:
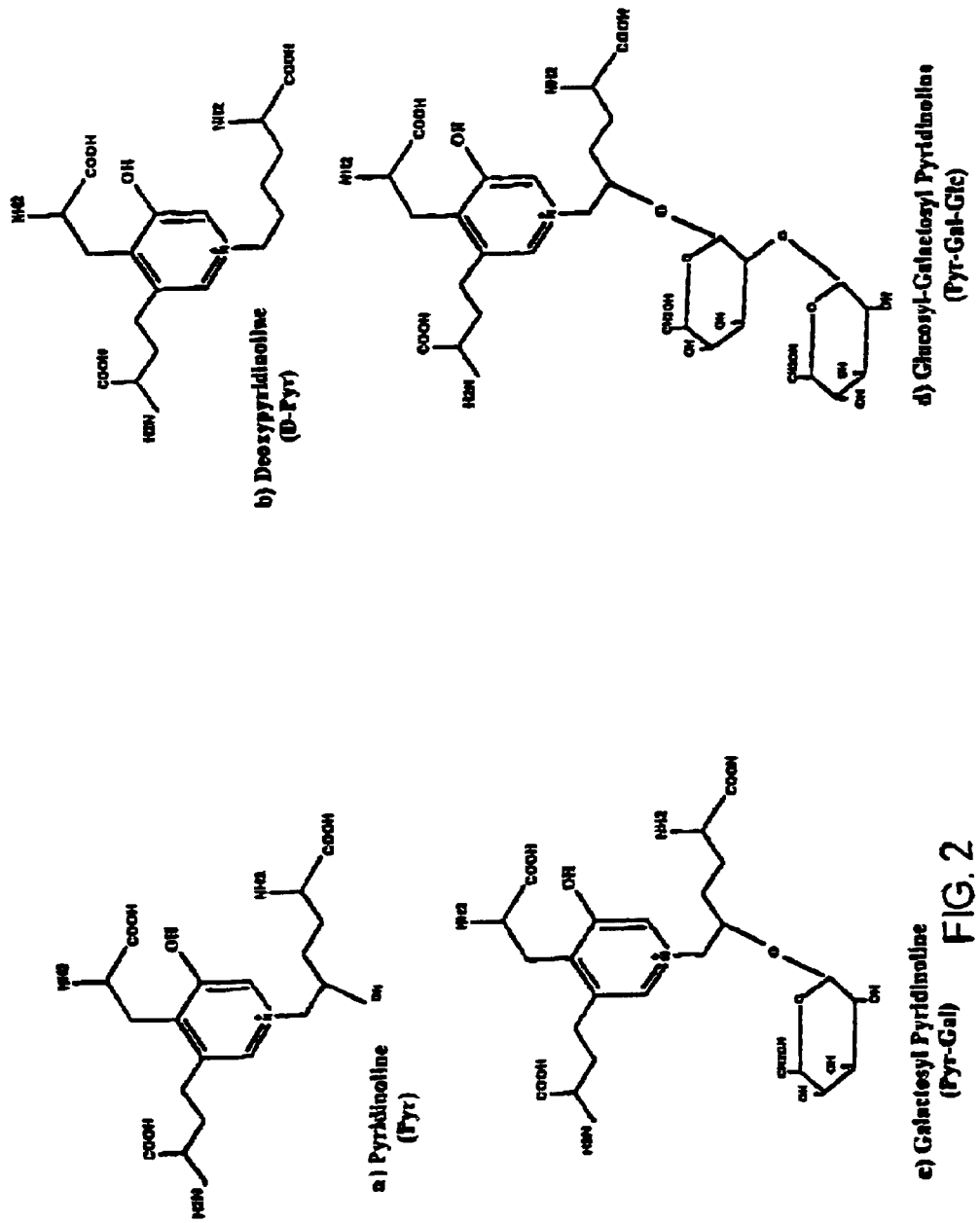
FIGS. 2a–d are chemical formulae of hydroxy- and deoxy forms of pyridinoline (Pyr) and deoxypyridinoline (D-Pyr) (a and b respectively), and glycosylated forms of pyridinoline (Pyr), namely galactosyl-pyridinoline (Pyr-Gal) and glucosyl-galactosyl-pyridinoline (Pyr-Gal-Glc) (c and d respectively).
Figure 3:
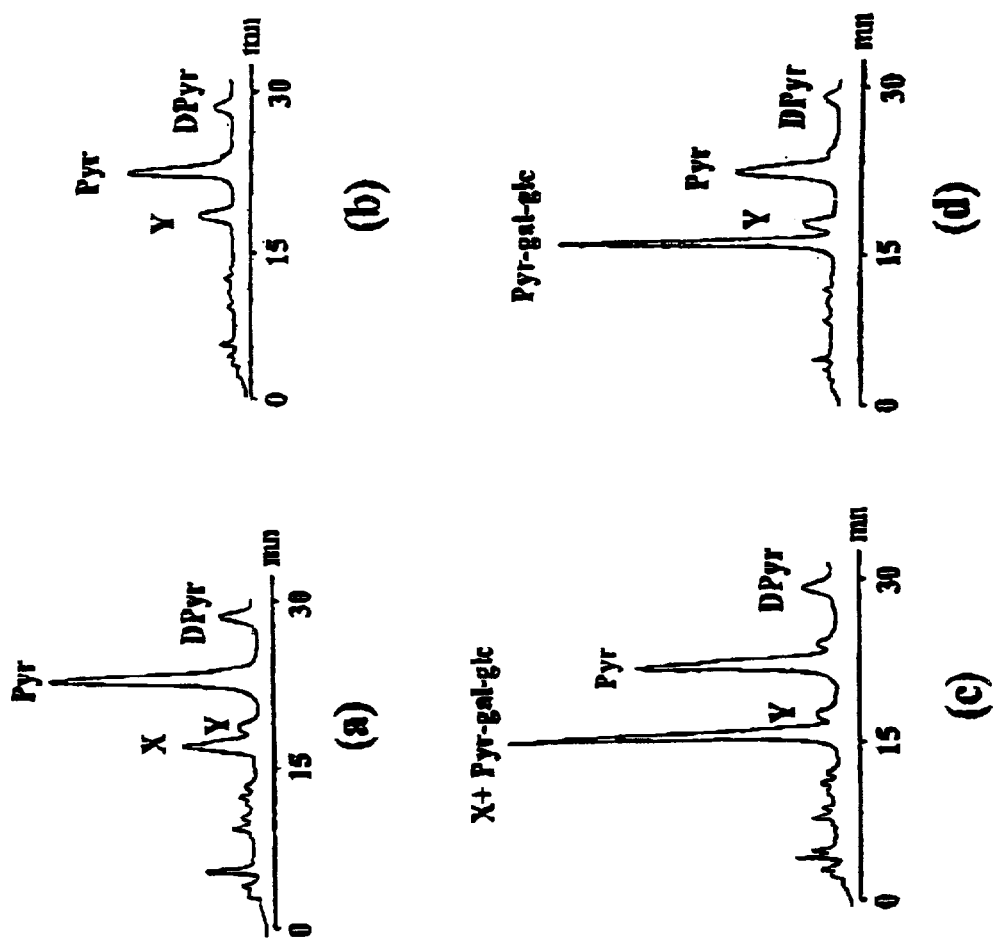
FIGS. 3a–d are chromatograms of human synovial tissue (a) and (c) and human bone tissue (b) and (d) treated by alkaline hydrolysis. For chromatograms (c) and (d), standard Pyr-Gal-Glc purified from urine was added to tissue samples used for chromatograms (a) and (b). Pyr and D-Pyr represent the hydroxy and deoxy forms of non glycosylated pyridinoline respectively. Compound X present in the synovial tissue but not in bone tissue co-migrates with standard Pyr-Gal-Glc purified from urine. Compound Y present in bone and in a very small quantity in synovial tissue does not co-migrate with standard Pyr-Gal-Glc purified from urine.
Figure 4:
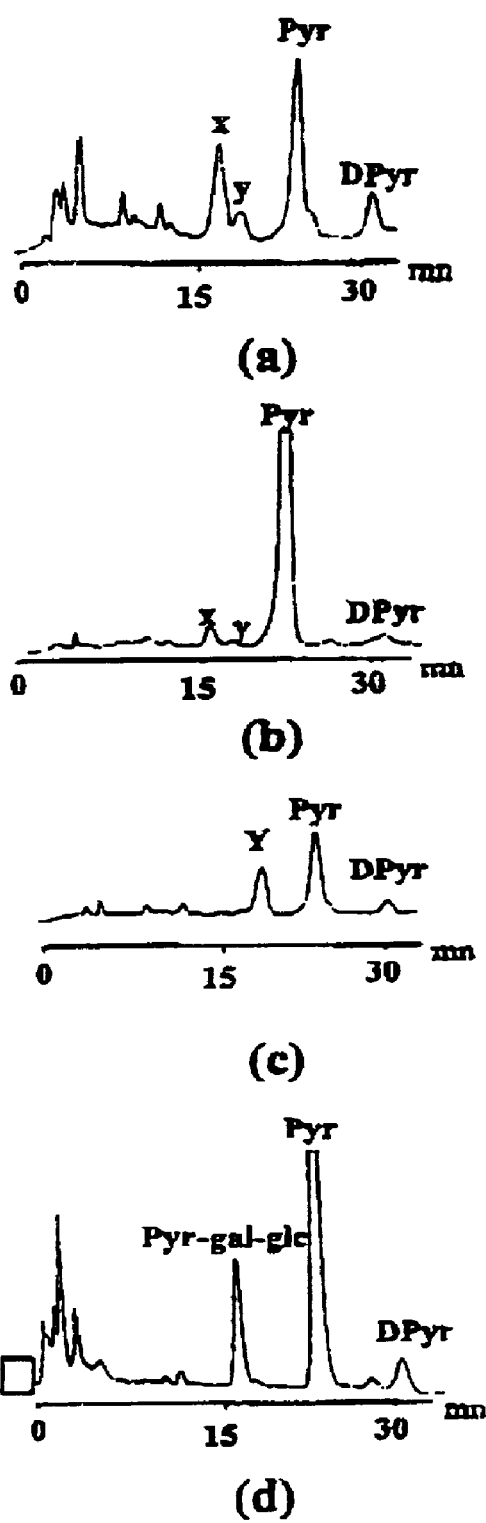
FIGS. 4a–d are chromatograms of human synovial tissue (a), human cartilage tissue (b) and human bone tissue (c) hydrolysed with 2M NaOH for 15 hours. Compounds X and Y are transformed into Pyr after acid hydrolysis and compound X co-migrates with standard Pyr-Gal-Glc purified from urine.

Results:

The chromatograms obtained from alkaline synovial hydrolysates (FIG. 3a) and alkaline bone hydrolysates (FIG. 3b) show the presence of two fluorescent compounds termed X and Y which eluted before non-glycosylated free pyridinoline (Pyr). After collection and acid hydrolysis, we were able to show that these two compounds are transformed into non-glycosylated free pyridinoline. Compound X, present in hydrolysates from synovial tissue and absent from bone tissue hydrolysates, co-migrated with the glucosyl-galactosyl-pyridinoline (Pyr-Gal-Glc) standard purified from urine (FIG. 3c). Compound Y, essentially present in hydrolysates from bone tissue and eluting just after the Pyr-Gal-Glc standard (FIG. 3d), corresponded to the mono glycosylated form of pyridinoline (Pyr-Gal). Cartilage contains little glycosylated pyridinoline (FIG. 4b). After 10 hours of hydrolysis, Pyr-Gal-Glc represented only 2% of the free Pyr (FIG. 5). Synovial tissue essentially contains Pyr-Gal-Glc. After 10 hours of hydrolysis, it represented 75% of the free Pyr (FIG. 5). Bone tissue essentially contains Pyr-Gal. After 10 hours of hydrolysis, it represented 39% of free Pyr (FIG. 6). It should also be noted that the percentage of glycosylated pyridinolines reduces with longer hydrolysis. This is probably linked to the fact that pyridinoline glycosylations are partially labile on alkaline hydrolysis. These experiments indicate that the type of glycosylated pyridinoline molecule differs in bone, synovial fluid and cartilage. In synovial fluid, glycosylation is of the Gal-Glc type; that of bone is of the Gal type; and the cartilage appears to be only slightly glycosylated.

Example 2

Pyridinoline Glycosylation Type Study in ex vivo Culture Model of Human Tissue Explants Methods:

Bone, cartilage and synovial tissue samples collected in a sterile manner during surgical interventions were placed in sterile pots containing PBS buffer (phosphate buffer saline) containing 100 U/ml of penicillin and 10 ng/ml of streptomycin (Gibco, Eragny, France), then transported rapidly to the laboratory. The three types of tissue were then separated from each other, and cut into cubes with sides of approximately 5 mm (about 125 mm$^3$) for the synovial fluid and the bone, and into slices about 1 mm thick with approximately 5 mm sides (about 25 mm$^3$) for the cartilage. The fragments were then placed in six-well plates (Falcon, CLV, Villeurbanne, France) containing 5 ml of RPMI 1640 culture medium (Gibco, Eragny, France) supplemented with 2% foetal calf serum (FCS) (Techgen, Les Ullis, France), 2 mM of glutamine (Gibco, Eragny, France), 20 mM of Hepes buffer (Gibco, Eragny, France), 100 U/ml of penicillin and 10 ng/ml of streptomycin (Techgen, Les Ullis, France). Interleukin 1 (IL-1) (Bachem, Bale Biochimie SARL, Voisins-le-Bretonneux, France) was added from the first day of bone and synovial explant culture in a concentration of 1 ng/ml of culture medium, and plasminogen was added in a concentration of 5 mM in addition to the IL-1 to the cartilage culture to activate the tissue degradation process. The containers were incubated at 37° C. at 95% humidity with 5% of $CO_2$ for seven days.

After 7 days of culture, the supernatants were filtered (Centrisart Cut-Off 5000, Sartorius) then analysed by HPLC using the technique described for Example 1.

Figure 7:
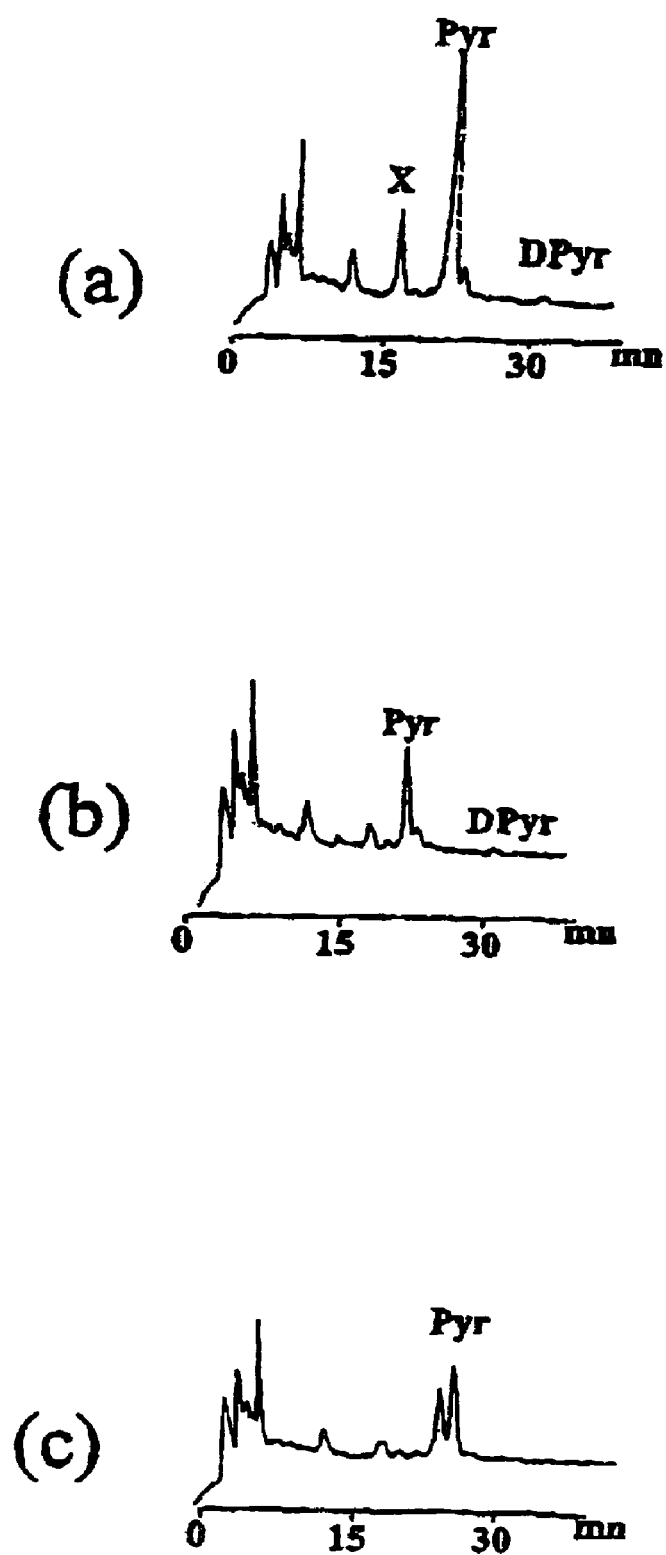

Results:

The chromatograms obtained from synovial tissue culture supernatants (FIG. 7a) show the presence of a fluorescent compound termed X which eluted before non glycosylated free pyridinoline (Pyr) and co-migrated with a Pyr-Gal-Glc standard purified from urine (FIG. 7d). After collection and acid hydrolysis, we were able to show that this compound was transformed into non-glycosylated free pyridinoline. This compound X present in synovial tissue culture supernatants was absent from bone tissue culture supernatants (FIGS. 7b and 7e). One compound co-migrating with the Pyr-Gal-Glc standard was found only in trace amounts in cartilage supernatants (FIGS. 7c and 7f). The quantities were too small to be able to determine whether it was in fact a form of pyridinoline.

These experiments confirm the results already obtained with alkaline hydrolysis of tissues in Example 1.

Example 3

Purification of Di-glycosylated Form of Pyridinoline

The diglycosylated form (Pyr-Gal-Glc) of pyridinoline was found in significant quantities in urine (FIG. 4d). Urine from children (2–13 years) is relatively rich in pyridinoline. We opted to purify diglycosylated pyridinoline from urine.

Method:

Purification of Diglycosylated Pyridinoline:

50 liters of child's urine was collected, filtered and freeze dried. The freeze-dried urine was dissolved in distilled water to obtain a 10-fold concentration of the urine. 500 ml of the concentrated urine was mixed with 500 ml of acetic acid, 2000 ml of n-butanol and 100 g of powdered cellulose (CFI, Whatman). It was mixed with a magnetic stirrer for 5 minutes then passed through a filter funnel to retain the cellulose. The cellulose recovered by filtration was washed with 12 liters of a washing solution containing 8 liters of n-butanol in 2 liters of acetic acid and 2 liters of distilled water. The operation was carried out in a series of 12 consecutive washes with 1 liter of solution. After washing, the pyridinoline molecules were eluted with 500 ml of distilled water and the eluate was freeze-dried. After freeze-drying, the eluates were dissolved in 10% acetic acid and deposited on a 2 liter Sephadex G10 (Pharmacia) gel filtration column. The fractions containing the diglycosylated pyridinoline were recovered and freeze dried. The freeze dried residue obtained was dissolved in 10% heptafluorobutyric acid and injected in 500 µl fractions onto a semi-preparative ultrasphere ODS C18 7 µ250×10 mm (Beckmann) reverse phase column. The Pyr-Gal-Glc molecules were eluted at a rate of 3 ml/minute with a 17% acetonitrile solution and 0.15% of heptafluorobutyric acid. Pyr-Gal-Glc molecules eluting between 15 and 20 minutes were collected, freeze-dried and stored at −30° C. All of these operations were repeated to treat all 50 liters of the child's urine.

Characterization by Mass Spectrometry

A 20 mg aliquot of Pyr-Gal-Glc was passed over a cation exchange column (cellulose phosphate cation exchanger, Sigma) to eliminate the heptafluorobutyric acid.

Reference should be made to general mass spectroscopic techniques for the mass spectrometric characterization.

Results:

The diglycosylated pyridinoline purification method described in this example was particularly advantageous as the cellulose passage step was carried out with a filter funnel instead of a cellulose column, and it was also carried out prior to the gel filtration step. The use of a filter funnel retaining the cellulose as the cellulose passage step and/or carrying out the gel filtration step after passage over cellulose are advantageous as these features, carried out separately or in combination, allow rapid purification and facilitate execution of the method. Such features save a great deal of time (about one week when purifying 50 l of urine) compared with purification techniques that do not have such features.

The diglycosylated pyridinoline was obtained in sufficient quantities to allow it to be used as an immunogen to produce monoclonal antibodies.

Example 4

Clinical Study of Urinary Excretion of Pyridinolines in Pre- and Post-menopausal Women and in Patients with Paget's Disease or Rheumatoid Arthritis Methods:

Urinary excretion of total pyridinoline and deoxypyridinoline was measured by HPLC after acid hydrolysis (or total hydrolysis) with 6N HCl. Urinary excretion of the free forms of pyridinoline (pyridinoline with no peptide) or free deoxypyridinoline (deoxypyridinoline with no peptide) was measured by HPLC, with no prior hydrolysis. The urinary concentration of CrossLaps (specific marker for bone resorption) (CrossLaps ELISA, Osteometer Biotech AS) and CartiLaps (specific marker for cartilage degradation) (CartiLaps ELISA, Osteometer Biotech AS) were analysed using ELISA.

Each of these markers was measured in:
i) 40 controls (pre-menopausal women and post-menopausal women);
ii) 27 patients with rheumatoid arthritis (RA);
iii) 10 patients with Paget's disease.

Results:

Urinary excretion of Pyr-Gal-Glc was significantly increased (100%) in patients presenting with rheumatoid arthritis (9.6±5.9) compared with the control group (4.7±1.4). while the increase (30%) observed in Paget's patients (6.1±1.9) was not significant (FIGS. 8 and 9). In contrast, the urinary concentrations of other analysed markers (total Pyr, total Dpyr, free Pyr, free DPyr, CrossLaps) were present in much higher quantities in Paget's patients than in patients with RA. Only the urinary excretion of CartiLaps (a marker for type II collagen degradation) was higher in RA patients (76%) compared with Paget's patients (4%). There was a significant correlation (p=0.0001) with a correlation coefficient of 0.80 between the concentrations of Pyr-Gal-Glc and of CartiLaps (FIG. 10). Patients presenting with RA were divided into two sub-groups: destructive RA (n=12) and non destructive RA (n=15). Urinary excretion of Pyr-Gal-Glc was higher in the destructive RA group compared with the non destructive RA group (FIG. 11). These results indicate that increased amounts of Pyr-Gal-Glc are associated with substantial joint destruction.

Example 5

Clinical Study of Urinary Excretion of Pyr-Gal-Glc in Patients with Gonarthrosis.

Method:
Urinary excretion of Pyr-Gal-Glc was measured by HPLC in 50 patients presenting with arthritis of the knee.
Results:
Urinary excretion of Pyr-Gal-Glc was correlated with the algofunctional indices of Lequesne (Lesquesne M et al., Scandinavian Journal of Rheumatology (1987) 18 (supplement 65), 85–9) and Womac (Bellamy N et al., Journal of Rheumatology (1988) 15, 1833–40) and the joint line (FIG. 12). The positive correlations obtained with the Lequesne index and the Womac index suggest that increased amounts of Pyr-Gal-Glc are associated with more pain and reduced mobility. The negative correlation obtained with the joint line indicated that increased amounts of Pyr-Gal-Glc are associated with greater cartilage destruction.

Example 6

Predictive Aspect of the Amount of Urinary Pyr-Gal-Glc in Patients with Rheumatoid Arthritis Method:
Urinary Pyr-Gal-Glc excretion was measured using HPLC in 112 patients having rheumatoid arthritis for less than three years. The amount measured at the start of the experiment was the base line for comparison.
Joint line narrowing, bone erosion and a total score corresponding to the combination of these two indicators were determined by X-ray radiography of the feet and hands (Sharp score) in all patients at the beginning of the study, after 6 months and after one year.
Results:
Patients with rheumatoid arthritis and at an early stage of the disease had higher urinary Pyr-Gal-Glc levels than in 64 healthy controls of the same sex and age, namely: 7.6 nmole/mmole of creatinin as opposed to 4.4 nmole/mmole of creatinin (p<0.0001) for the controls.
The table in FIG. 13 shows the results of a longitudinal study carried out over one year. The 112 patients were examined for aggravation of the disease on the basis of three indicators, namely joint space narrowing, bone erosion and a combination of these two (total score). In the event of progression of articular destruction on the basis of indicator change, the patient was classified into a "yes" column for that indicator, and in the other column for the opposite case.
Analysis of the results clearly shows that patients with X ray radiographs showing a progression in articular destruction over one year had raised base levels of urinary Pyr-Gal-Glc. Patients in whom the Pyr-Gal-Glc levels were higher than the mean level in healthy subjects by two standard deviations (i.e., 39% of the population) ran an increased risk of progression of the articular disease with an odds ratio of 3.6 (1.5–8.1) [confidence interval: 95%]. The results of the study clearly indicate that a high level of Pyr-Gal-Glc is associated with an increased risk of rapid joint destruction evaluated over one year, for early stage rheumatoid arthritis.

What is claimed is:

1. A method for monitoring the evolution of a synovial disease, comprising:
   i) bringing a biological sample from an individual into contact, in vitro, with a means for measuring a specific marker for synovial disease, said specific marker being diglycosylated pyridinoline;
   ii) determining the level of the specific marker;
   iii) comparing the level of the marker with a reference level of the specific marker, wherein the reference level is a previously measured level in the same individual, the level of the marker with respect to the reference level indicating the evolution of the synovial disease.

2. The method of claim 1, wherein said determination of the level of the specific marker for synovial disease is carried out by an immunological technique, by immunoassay, by fluorescence, by ultraviolet spectroscopy or by electrochemical detection.

3. The method of claim 2, wherein said immunological technique is a technique employing specific monoclonal or polyclonal antibodies, an ELISA technique, an immunoenzymatic technique, an immunofluorescent technique, a radio-immunological technique or a chemo-immunological technique.

4. The method of claim 1, wherein the level of the specific marker for synovial disease is determined by an High Performance Liquid Chromatography technique.

5. The method of claim 1, wherein the biological sample is a body fluid.

6. The method of claim 5, wherein said body fluid is selected from blood, serum, plasma, urine, saliva, sweat and synovial fluid.

7. A method for diagnosing a synovial disease comprising:
   i) bringing a biological sample from an individual into contact, in vitro, with a means for measuring a specific marker for synovial disease, said specific marker being diglycosylated pyridinoline;
   ii) determining the level of the specific marker;
   iii) comparing the level of the marker with a reference level of the specific marker representing the absence of the disease, wherein an increased level of the marker with respect to the reference level indicates the presence of the synovial disease.

8. The method of claim 7, wherein said determination of the level of the specific marker for synovial disease is carried out by an immunological technique, by immunoassay, by fluorescence, by ultraviolet spectroscopy or by electrochemical detection.

9. The method of claim 8, wherein said immunological technique is a technique employing specific monoclonal or polyclonal antibodies, an ELISA technique, an immunoenzymatic technique, an immunofluorescence technique, a radio-immunological technique or a chemo-immunological technique.

10. The method of claim 8, wherein the level of the specific marker for synovial disease is determined by an High Performance Liquid Chromatography technique.

11. The method of claim 8, wherein said reference level is selected to be in the range from about 5 nmole/nmole creatinin to about 9 nmole/nmole creatinin.

12. The method of claim 8, wherein the biological sample is a body fluid.

13. The method of claim 12, wherein said body fluid is selected from blood, serum, plasma, urine, saliva, sweat or synovial fluid.

* * * * *